United States Patent [19]

Hodson et al.

[11] Patent Number: 4,801,593

[45] Date of Patent: Jan. 31, 1989

[54] CHEMOTHERAPEUTIC AGENTS

[75] Inventors: Harold F. Hodson; John F. Batchelor, both of Beckenham; John W. T. Selway, Cranbrook; Jeremy G. Vinter, Dorking; Ramachanderan Iyer, Beckenham, all of United Kingdom

[73] Assignee: Burroughs Wellcome Co., Research Triangle Park, N.C.

[21] Appl. No.: 177,125

[22] Filed: Aug. 11, 1980

[30] Foreign Application Priority Data

Sep. 13, 1979 [GB] United Kingdom ................ 7931839

[51] Int. Cl.$^4$ .................... A61K 31/47; A61K 31/38
[52] U.S. Cl. .................................... 514/307; 514/310; 514/311; 514/432
[58] Field of Search ................ 424/258; 514/310, 307, 514/311, 432

[56] References Cited

U.S. PATENT DOCUMENTS 3,332,951 7/1967 Rossi et al. .
3,755,372 8/1973 Irmscher et al. .

OTHER PUBLICATIONS

Reed et al., Jof Infectious Diseases, vol. 133, Jun. 1976, pp. 128–135.
Beeby et al. J. Chem. Soc. (1949), 1799–1803.
Ferreira et al., J. Chem. Soc. Perkin Trans. I (1974) (21), 2429.
Gnanamanickam et al., Physiol. Plant. Pathol. (1977), 10, 159–168.
Farrington. Diss. Abstr. Int. B 1974, 34(21), 5899.
Gogte et al. Ind. J. Chem. (1974), 12, 1234–7.
van Binst et al. Bull Soc. Chim. Belg. (1976), 85, 1.
Archer et al. J. Chem. Soc. (1964) 249.
Rieche et al. Chem. Berichte 97(1), (1964), 195.
Braun and Manz. Ann. 468, 258–77 (1929).
Keuchi Shishido and Joshio Jashikawa. J. Am. Chem. Soc. 70, 1608–9 (1948).
Keuchi Shishido and Hajime Lozaki. J. Soc. Chem. Ind. Japan 48 49 (1945).
Keuchi Shishido and Hajime Lozaki. J. Soc. Chem. Ind. Japan 49 141 (1946).
Protiva et al. Collection Czech. Chem. Communs. 15 532–40 (1950).
Auramoff and Sprinzak J. Am. Chem. Soc. 78 4090–6 (1956).
Klosa Arch. Pharm. 289 177–88 (1956).
Cromwell and Mercer J. Am. Chem. Soc. 79 3815–18 (1957).
Gutsche et al. J. Am. Chem. Soc. 80 5756–67 (1958).
Neumann Ann. 618 a 90–105 (1958).
Sidorov Ser Khim (1961) No. 38 132–41.
Rieche and Hoeft J. Prakt. Chem. 17 293–8 (1962).
Belgian Patent No. 617,438.
Booth J. Chem. Soc. 1964 (May) 1841–7.
French Patent No. 1,326,722.
Naoto Inoue Bull. Chem. Soc. Japan 37(5) 601–5 (1964).
Bijan Prasun Das Indian J. Chem. 3(6) 268–70 (1965).
Belgian Patent No. 641,254.
Kurosato K et al. Chem. Commun. 1968 (20) 1265–7.
Gogte V. N. et al. Tetrahedron Lett. 1969 (39) 3319–22.
Gverdtsiteli et al. Izv. Akad. Nauk SSSR Ser. Khim 1970 (6) 1240–4.
Dann et al. Jushis Liebigs Ann. Chem. 1972 760 37–87.
Weil R et al. C. R. Acad. Sci. Ser C 1972 275(4) 299–301.
Eisenbraun E. J. et al. Amer. Chem. Soc. Div. Petrol Chem. Prepr. 1971 16(3) B43–B50.
Kattaev et al. Khum. Priv. Soedin 1975 11(2) 147–52.
Yamamura Shiro et al. Chem. Pharm. Bull. 1976 24(12) 3222–5.
Szabo and Antal Acta. Chim. Acad. Sci. Hung. 1976 90 (4) 381–93.
UK Patent Specification No. 1,546,296.
Jung and Mossman and Lyster J. Org. Chem. 1978 43(19) 3698–701.
Kurosawa K. et al. Phytochemistry 1978 17(8) 1423–6.
Elslager E. F. et al. J. Med. Chem. 15(8) 827–36 1972.
Kauffmann Macromol. Chem. 180(11) 2649–63 (1979).
Weil and Collignon Bull. Soc. Chun. Fr. 1974 1–2 pt 2 258–62.

Primary Examiner—Jerome D. Goldberg
Attorney, Agent, or Firm—Donald Brown

[57] ABSTRACT

A method of treating or preventing viral infections, in particular rhinovirus infections comprising the administration of an effective amount of a 2-phenyltetralin derivative or a heterocyclic analogue thereof. Pharmaceutical compositions containing these compounds, and some novel compounds are also disclosed.

18 Claims, No Drawings

CHEMOTHERAPEUTIC AGENTS

The present invention relates to certain 2-phenyltetralin derivatives and heterocyclic analogues thereof which are useful as medicaments. In particular such compounds are antiviral agents, and are especially suitable for the prevention and treatment of rhinoviral infections. The invention also relates to processes for the production of these compounds, to pharmaceutical formulations containing them and to methods of treatment employing them.

In the majority of instances, the disease known as the "common cold" is caused by rhinoviral infections, although "colds" may also be caused by infection of the upper respiratory tract by e.g. corona and enteroviruses and allergic reactions may be mistaken for colds. Mankind throughout the world is prone to rhinoviral infections, which are a major cause of absence from work through illness. The prevention and treatment of such diseases is thus of great economic importance.

Once infected by a rhinovirus, an individual retains immunity to that serotype, which may be enhanced by continual reinfection if the serotype is prevalent in the community. There is however, no cross-immunity between serotypes and thus a cold is usually experienced by an individual whenever a new serotype of rhinovirus is encountered, on average about twice or three times a year.

Immunisation against rhinovirus is not practicable because there are about 120 known serotypes of rhinovirus and a vaccine against all these would overload the vaccinee's immune system.

It would therefore appear that chemotherapy is the only suitable method for preventing or treating rhinoviral infections. Much research effort has been expended in recent years but no effective chemotherapeutic agent has yet emerged.

It has now been found that certain 2-phenyltetralin derivatives, and heterocyclic analogues thereof, are active against rhinoviruses.

According to the present invention therefore, there is provided a compound of formula (I):

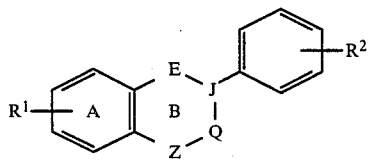

(I)

as a medicament, or in a pharmaceutically acceptable formulation wherein

E is a sulphur atom or a NH or $CH_2$ group,

J is a nitrogen atom or a CH group,

Q is a sulphur atom or a $NR^3$ or $CHR^3$ group and

Z is an oxygen or sulphur atom or a $NR^4$ or $CHR^4$ group and $R^1$ represents four substituents and $R^2$ represents five substituents, each of said substituents being selected from hydrogen or halogen atoms, (lower)alkyl, hydroxy (lower) alkyl, carboxy(lower)alkyl, (lower)alkoxyl, amino, (lower)alkylamino, di(-lower) alkylamino, acylamino, nitro, cyano, trifluoromethyl, carboxyl, methylenedioxy and hydroxyl groups and whenever present, $R^3$ and/or $R^4$ are each selected from (lower) alkyl groups and hydrogen atoms, and salts or esters of such compounds, whenever appropriate provided that at least three of E, J, Q and Z are methylene residues.

$R^1$ and $R^2$ can represent the same or different substituents, each of the substituents $R^1$ represents can be independently selected from the aforementioned list of atoms or groups and can be different from the substituents $R^2$ represents which also can be independently selected.

It will be noticed that formula (I) thus embraces the following types of compounds:
substituted or unsubstituted 2-phenyl-1,2,3,4-tetrahydronaphthlene (i.e. 2-phenyltetralin)
substituted or unsubstituted 2- and 3-phenyl-1-thiochroman (i.e. thioflavan and isothioflavan)
substituted or unsubstituted 2-thio-3-phenyltetralin
substituted or unsubstituted 3-phenylchroman (i,e. isoflavan)
substituted or unsubstituted 2- and 3-phenyl-1,2,3,4-tetrahydroquinoline
substituted or unsubstituted 2- and 3-phenyl-1,2,3,4-tetrahydroisquinoline Such a compound is particularly suitable for use in the treatment or prevention of viral, especially rhinoviral, diseases.

Of these, 2-phenyltetralin, 2-phenyl-1-thio chroman, and 2-phenyl-1,2,3,4-tetrahydroisoquinoline and derivatives thereof, are preferred.

As used herein the expression "(lower)alkyl" and "(lower)alkoxy" and cognate terms, mean straight or branched chain alkyl or alkoxyl groups having 1 to 4 carbon atoms.

As used herein the expression "acyl amino" means an amino group substituted with the residue of a carboxylic acid, in particular a (lower)alkyl, aryl(lower) alkyl or aryl carboxylic acid.

Whenever a compound of formula (I) bears a hydroxyl, amino or carboxyl group, or has a nitrogen atom in the "B" ring, salts and esters may be formed, and these are encompassed within the present invention. It is preferred that these salts and esters be pharmaceutically acceptable. A discussion of the properties and desirability of various salts is given in "pharmaceutical salts" by S. M. Berge et al, *J. Pharm. Sci.*, 66,1, (1977).

It will be appreciated that most of the compounds of formula (I) may exist in various stereoisomeric forms, all of which are encompassed by the present invention. In particular, whenever J is a methylene residue, the compound will exist in two enantiometric forms, as it will whenever Q or Z contains an asymmetic carbon atom, and diastereomeric forms will arise when there are two or three asymmetric carbon atoms in the compound.

Whenever J and Q are methylene derivatives and $R^3$ is other than a hydrogen atom, it is preferred that the phenyl group at the 2-position and $R^3$ be in the transconfiguration.

It is preferred that, whenever present, $R^3$ and $R^4$ are each a hydrogen atom or a (lower)alkyl group, in particular a hydrogen atom or a methyl group, and it is most preferred that $R^3$ and $R^4$ are each a hydrogen atom.

Whilst $R^1$ may represent up to four atoms or groups other than hydrogen atoms, it is preferred that at least two of the substituents represented by $R^1$ are hydrogen atoms. More preferably $R^1$ represents at least three hydrogen atoms.

Similarly, it is preferred that at least three of the substituents represented by $R^2$ are hydrogen atoms.

Of the (lower)alkyl and (lower)alkoxyl groups, those having from 1 to 3 carbon atoms are preferred.

Particularly preferred substituents are hydrogen and halogen atoms, and amino, hydroxyl, methyl, ethyl, methoxyl, ethoxyl, hydroxymethyl, trifluoromethyl, and cyano groups.

It is preferred that substituents other than hydrogen atoms represented by $R^1$ are located at the 6, and/or 7 positions of a compound of formula (I), most preferably at the 6 position and that substituents other than hydrogen atoms represented by $R^2$ are located at the 3', 4' and/or 5' positions, most preferably at the 4' position.

Compounds of formula (I) are more preferred as medicaments or in pharmaceutically acceptable formulations, when they conform to formula (IA)

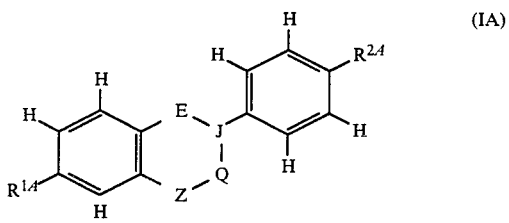

(IA)

wherein E, J, Q and Z are as hereinbefore defined and $R^{1A}$ and $R^{2A}$ each represent a single substituent selected from the class defined with respect to $R^1$ and $R^2$. Compounds of formula (I) and especially of formula (IA) representing a conjunction of two or more of the preferences stated hereinbefore are particularly preferred embodiments.

The most preferred compounds of formula (I) as medicaments or in pharmaceutical formulations are the following, namely.

Thioflavan
4'-chlorothioflavan
6-chlorothioflavan
4',6-dichlorothioflavan
2-phenyl-1,2,3,4-tetrahydroquinoline
2-(4-chlorophenyl)-1,2,3,4-tetrahydroquinoline
6-chloro-2-phenyl-1,2,3,4-tetrahydroquinoline
6-chloro-2-(4-chlorophenyl)-1,2,3,4-tetrahydroquinoline
2-phenyl-1,2,3,4-tetrahydroisoquinoline
2-(4-chlorophenyl)-1,2,3,4-tetrahydroisoquinoline
6-chloro-2-(4-chlorophenyl)-1,2,3,4-tetrahydroisoquinoline
2-phenyltetralin
3-phenyl-1,2,3,4-tetrahydroquinoline
3-(4-chlorophenyl)-1,2,3,4-tetrahydroquinoline
6-chloro-3-phenyl-1,2,3,4-tetrahydroquinoline
6-chloro-3-(4-chlorophenyl)-1,2,3,4-tetrahydroquinoline
3-phenyl-1,2,3,4-tetrahydroisoquinoline
3-(4-chlorophenyl)-1.2.3.4-tetrahydroisoquinoline
6-chloro-3-phenyl-1,2,3,4-tetrahydroisoquinoline
6-chloro-3-(4-chlorophenyl)-1,2,3,4-tetrahydroisoquinoline
3-phenylchroman
3-(4-chlorophenyl)chroman
6-chloro-3-phenylchroman
6-chloro-3-(4-chlorophenyl)chroman According to a second aspect of the present invention there is provided a novel compound of formula (II)

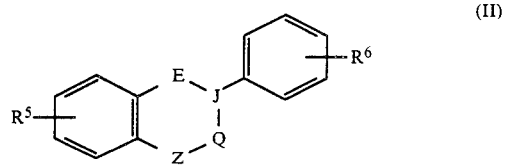

(II)

wherein $R^5$, $R^6$ are as hereinbefore defined with respect to $R^1$ and $R^2$, and E, J, Q and Z are as hereinbefore defined or a salt or ester thereof, where appropriate except for the following known compounds namely:

2-phenyl-1,2,3,4-tetrahydroquinoline
3-phenyl-1,2,3,4-tetrahydroquinoline
2-phenyltetralin
2-phenyl-1,2,3,4-tetrahydroisoquinoline
3-phenyl-1,2,3,4-tetrahydroisoquinoline.
3-phenyl-chroman
3-phenyl-7-methoxychroman and also excluding any derivative of 3-phenylchroman which bears two or more substituents selected from methoxyl, ethoxyl, methylenedioxy and hydroxy groups, and the acetate esters of the latter, one of the substituents being located at the 7-position and a second being located on the phenyl group, unless that derivative also bears a (lower)alkyl, hydroxy(lower)alkyl, carboxy(lower)alkyl, amino, (lower)alkylamino, di(lower)alkylamino, acylamino, nitro, cyano, trifluoromethyl or, carboxyl group or a halogen atom Compounds of formulae (I) and (II) are produced by a variety of processes, which are analogous to the methods which are known and used in the art of synthesis of benzoheterocyclic and benzoalicyclic compounds.

2-Phenyltetralin, its derivatives and heterocyclic analogues thereof may be prepared by the reduction of double bonds in, or of substituent groups on the "B" ring (as shown in formula (I)). Thus, (a), 2-phenyltetralins and their analogues, which bear, on the "B" ring, oxo, hydroxy, mercapto or halogeno substituents may be reduced by methods such as the Clemmensen reduction and by catalytic or chemical reduction of double bonds in the 1,2; 2,3 or 3,4 positions, as appropriate. Exocyclic double bonds and other reducable moieties in precursors for $R^3$ and/or $R^4$, such as alkenyl and alkylidene groups, may also be reduced to afford compounds of formulae (I) and (II).

When the compound of formula (I) contains a sulphur atom it is possible that it will poison catalysts used for catalytic reduction, but this may be overcome by choosing suitable catalysts or using larger quantities of catalyst.

Alternatively, (b), the compounds of formula (I) and (II) are obtained by cyclisation reactions in which the "B" ring is produced.

Those compounds of formula (I) having a heteroatom in the 2 or 3 position can be produced by condensation reactions in which the "B" ring is formed. Thus 2- and 3-phenylisoquinolines and isothioflavans are produced by ring closure reactions in which a bond is formed between the heteroatom and an adjacent carbon atom. Accordingly, the 2-phenyl isoquinolines are produced, for instance, by reaction of an aniline with an 2-(2-chloroethyl)benzyl chloride derivative, whilst condensation of a 2-(2-chloro-2-phenylethyl)benzyl chloride derivative with ammonia affords a 3-phenylisoquinoline, and with hydrogen sulphide or sodium sulphide may afford an isothioflavan derivative.

Where appropriate, when preparing compounds of formula (I) which may exist in cis and trans forms, particular attention should be paid to the stereochemistry of the reactions employed, since some are more suitable for obtaining cis isomers and others are better adapted to the production of the trans isomers. Obviously not all the reactions are stereospecific or stereoselective and in these cases, separation steps such as chromatography may be required in order to obtain a particular geometric isomer in a pure form.

By selecting a particular enantiomer of a starting material and using an asymmetric synthesis, an optically pure enantiomer of a compound of formula (I) may be obtained (e.g. Corey & Mitra, *J. Am. Chem. Soc.*, 84, 2983, (1962)). Alternatively, where suitable, resolution of a compound of formula (I) may be possible by the use of asymmetric reagents or chromatographic media.

Once the 2-phenyltetralin ring system, or a heterocyclic analogue thereof, has been produced, further compounds of formula (I) and (II) may be obtained by addition, replacement, modification or elimination of the substituents on the aromatic rings, although it is usually more convenient to use starting materials which already bear the requisite substituents.

When a substituent such as a hydroxyl or amino group may be altered by, or indeed could interfere with the desired synthetic process, it may, of course, be blocked by conventional means such as acylation and later deblocked to afford the desired compound of formula (I) or (II).

Salts and esters, where appropriate, of compounds of formula (I) or (II) may be produced by standard chemical processes such as metathetical reactions.

The compounds used as starting materials for the production of 2-phenyltetralins or heterocyclic analogues thereof of formulae (I) and (II) may be obtained commercially or prepared by standard chemical means.

The literature references given below illustrate some of the techniques which may be applied in the production of benzoheterocyclic and benzoalicyclic compounds and in some cases disclose compounds which may be used as immediate precursors in the preparation of compounds of formula (I).

Katekar, *Austral. J. Chem.*, 19(7), 1251, (1966)
Degani, et al., *Ann. Chim.* (Rome), 61(12), 793, (1971)
Cotterill, et al., *J. Chem. Soc.* (Perkin trans. I), 817, (1972)
British Patent Specification No. 1483 093
Chauhan & Still, *Can. J. Chem.*, 53, 2881, (1975)
Inoue, *Bull. Chem. Soc. Japan*, 37(5), 601, (1964) (C.A., 5601c, (1964))
Szabo & Antal, *Acta Chim. Acad. Sci. Hung.*, 90, 381, (1976)
J. B. Harborne, T. J. Mabry and H. Mabry (Eds), "The Flavanoids", Chapman and Hall, London, 1975, especially pp 184 et seq.
E. L. Martin, *Organic Reactions*, 1, 161, (1942)
E. Vedejs, *Organic Reactions*, 22, 412, (1974)
B. L. Verma, et al., *Indian J. Chem.*, 3(12), 565, (1965)
M. M. Bokadia & B. L. Verma, *Chem. and Ind.*, 235, (1964)
E. J. Keogh, et al., *Chem. and Ind.*, 2100, (1961)
Nielson, *Organic Reactions*, 16, 44, (1968)
Riech & Schmitz, *Chem. Ber.*, 89, 1254, (1956)
Rieche et al., *Ber.*, 94, 544, (1961)
Rieche & Hoft, *J. Prakt. Chem.*, 17, 297, (1962)
Ungnade et al., *J. Org. Chem.*, 533, (1945)
Gabriel & Posner, *Ber.*, 27, 2506, (1894)
Berti, *Tetrahedron*, 393, (1958).

While it is possible for the compounds of formula (I) or (II) or, where appropriate, pharmaceutically acceptable salts thereof (hereinafter referred to as the "active compounds") to be administered as the raw chemical it is preferred that the active compound is presented in the form of a pharmaceutical composition.

In a further aspect of the invention there is therefore provided a pharmaceutical formulation comprising the active compound together with a pharmaceutically acceptable carrier therefor. The carrier must be "acceptable" in the sense of being compatible with the other ingredients of the formulation and not deleterious to the recipient thereof. Such carriers are solid, liquid or gaseous materials recommended for the purpose of administering the medicament.

The terms "formulation" and "composition" are used herein synonomously.

These pharmaceutical compositions may be administered orally or parenterally (including subcutaneous, intramuscular and intravenous injection) or as a suppository or pessary or may be applied topically or as an ophthalmic solution, or may be inhaled. It is preferred that the compositions are administered orally or inhaled.

For oral administration the pharmaceutical compositions may be presented as a draught in water or in a syrup, in capsules, cachets, boluses or tablets, as an aqueous or oleaginous solution or suspension or in suspension in a syrup, such suspensions optionally including suspending agents or as an oil-in-water or water-in-oil emulsion. Where desirable or necessary flavouring, sweetening, preserving, thickening or emulsifying agents may be included in the formulation.

Tablets may contain the active compound as a powder or granules optionally mixed with binders, lubricants or inert diluents or surface-active or dispersing agents and may be formed by compression or by moulding in an inert liquid diluent. Such tablets may be optionally scored and/or coated.

Capsules and cachets may contain the active compound alone or in admixture with one or more accessary ingredients. Capsules may also contain the active compound in aqueous or oleaginous solution suspension or emulsion, optionally in association with accessory ingredients.

For administration as a suppository or pessary the active compound may be presented in admixture with a suitable carrier such as cocoa butter and other material commonly used in the art, the formulation conveniently being shaped by moulding.

For administration in discrete dosage forms such as the tablets, capsules, suppositories and pessaries described above, the active compound is preferably presented at 0.1 mg to 100 mg most preferably 1 mg to 10 mg per tablet, casule, suppository or pessary.

For parenteral administration the active compound may be presented in sterile solutions or suspensions in aqueous or oleaginous vehicles, which may also contain preservatives and materials for rendering the solution or suspension isotonic with the blood of the intended recipient. Such formulations may conveniently be presented in unit-dose or multi-dose sealed containers.

For topical administration the composition may be presented in ointments creams lotions, pastes, jellies, sprays, aerosols and bath oils. Ointments and creams may have oleaginous, absorption and colloidal clay bases and may contain thickening agents such as gum tragacanth or sodium alginate and other pharmaceutically acceptable accessory ingredients such as humectants, preservatives, buffers and antioxidants which are useful in such formulations.

For administration as eye drops, the active compound is presented in sterile water with excipients such as antimicrobical agents and antioxidants, as a dilute solution.

For administration orally in liquid form or parenterally or as eye drops the active compound is preferably presented in solution or suspension or emulsion at a concentration of from 0.1 to 10%, more preferably 0.2 to 5% w/v in unit or multi-dose forms. When presented in unit dose form it is preferred that each dose unit contains 0.1 mg to 100 mg, preferably 1 mg to 10 mg of active compound.

For inhalation the active compound may be presented in association with volatile excipients, as a cream, lotion, paste or ointment or as a finely divided dry powder or in solution for inhalation through a nasal spray, atomiser or insufflator.

All the above formulations are produced by processes which comprise bringing into association the active compound and one or more carriers.

According to the present invention there is therefore provided a process for producing a pharmaceutical formulation of a compound of formula (I) comprising bringing into association a compound of formula (I) and a pharmaceutiallly acceptable carrier therefor.

Compounds of formula (I) may be administered to human beings and to other animals to treat or prevent viral diseases, especially rhinoviral infection. The dosage administered obviously depends on the activity of the active compound and also on the speed with which it is absorbed into the body and on other well-known pharmacological considerations, however it is recommended that the active compound is administered at from 2 µg to 10 mg/kg of animal body weight per day, preferably from 25 µg to 1 mg/kg/day and most preferably about 0.1 to 0.3 mg/kg/day. The active compound may be administered once or several times daily to achieve the required daily dose.

In a further aspect of the present invention there is therefore provided a method for treating rhinoviral infections comprising the administration, in an effective dosage, a compound of formula (I) or a pharmaceutical formulation thereof to a human being or other animal.

In a yet further aspect of the present invention there is provided a method for preventing rhinoviral infections comprising the administration in an effective dosage a compound of formula (I) of a pharmaceutical formulation thereof, to an apparently healthy human being or other animal.

As used herein the term "effective dosage" means that quantity of a compound of formula (I) which is sufficient to cure or prevent a rhinoviral infection.

The invention will now be illustrated with reference to the following Examples, which are not intended to limit the invention in any way.

Temperatures are given hereunder in degrees Celsius. Pressures are given hereunder in millimeters of mercury ("mmHg"). (1 mm Hg=133.322 Pa).

EXAMPLE I

Preparation of thioflavan (a) Cinnamic acid (30.0 g.), benzenethiol (24.0 g.) and 45% w/v hydrogen bromide in acetic acid (21.5 ml) were heated together at 100° for 7 hrs. The reaction mixture was diluted with water and steam distilled to remove unchanged thiol. The hot aqueous layer was decanted from the oily product, which was recrystallised from 60°–80° petrleum ether to give 3-phenyl-3-(phenylthio)propionic acid (36.7 g) m.pt. 85°–90°. A sample recrystallised again from 60°–80° petroleum ether had m.pt. 88°–90°.

(b) 3-Phenyl-3-(phenylthio)propionic acid (60.0 g) was boiled under reflux with thionyl chloride (240 ml). for 30 min. The excess thionyl chloride was evaporated off and the residual acid chloride dissolved in nitrobenzene (240 ml.) and added to a stirred suspension of aluminium chloride (68.4 g) in nitrobenzene (600 ml) over 20 min. The mixture was stirred at room temperature for 2 hr., then poured on to ice and excess hydrochloric acid. The mixture was steam distilled to remove the nitrobenzene and the residue extracted into chloroform, dried and evaporated. The residue was chromatographed in silica gel, eluting with chloroform, to give thioflavanone (27.8 g.) m.pt. 48°–57°, (57°–58° after recrystallisation from ethanol).

(c) Thioflavanone (10.0 g) was dissolved in acetic acid (300 ml) and concentrated hydrochloric acid (30 ml) and added to zinc amalgam prepared from zinc powder (100 g.) and mercuric chloride (8.0 g.) The reaction mixture was stirred at room temperature for 3 hr., then allowed to stand overnight. The reaction mixture was filtered and the filtrate diluted with water and extracted with toluene. The toluene extract was washed with water, dried and evaporated. Trituration of the residue with ethanol gave, on filtration, thioflavan (2.55 g) m.pt. 45°–49°-Recrystallisation of a sample from ethanol gave pure thioflavan m.pt 55°–56°.

Microanalysis: Theory: C: 79.60% H: 6.23%; Found: C: 79.97% H: 6.21%.

EXAMPLE 2

Preparation of 4'-chlorothioflavan (a) 3-(4-Chlorophenyl)-3-(phenylthio)propionic acid, m.pt. 99°–102° (ex cyclohexane) was prepared from benzenethiol and p-chlorocinnamic acid by a method exactly analogous to that used in Example 1(a)

(b) 3-(4-Chlorophenyl)-3-(phenylthio)propionic acid (47.6 g.) was heated at 100° with phosphoryl chloride (400 ml.) for 2 hr. The reaction mixture was cautiously decomposed by addition to water, and the product extracted into toluene. The extract was washed with 2-M sodium hydroxide solution and water, dried and evaporated. Recrystallisation of the residue from ethanol gave 4'-chlorothioflavanone (17.0 g) m.pt. 116°–120°. (m.pt. 125°–126° after two further recrystallisations from ethanol)

(c) 4'-Chlorothioflavan, m.pt 109°–110° was prepared from 4'-chlorothioflavanone by a method exactly analogous to that used in Example 1(c).

Microanalysis: Theory: C: 69.08% H: 5.02%; Found: C: 69.40% H: 4.92%.

EXAMPLE 3

Preparation of 4',6-dichlorothioflavan (a) 3-(4-Chlorophenyl)-3-(4-chlorophenylthio)propionic acid (m.pt. 146°–148°), was prepared from p-chlorobenene thiol and p-chlorocinnammic acid using a method exactly analogous to that used in Example 1(a)

(b) 4',6-dichlorothioflavanone, (m.pt. 109°–111°), was prepared from 3-(4-chlorophenyl)-3-(4-chlorophenylthio)propionic acid by a method exactly analogous to that used in Example 2(b)

(c) 4',6-dichlorothioflavanone, (m.pt. 125°–127°), was prepared from 4',6-dichloroflavanone by a method exactly analogous to that used in Example 1(c).

Microanalysis: Theory: C: 61.03% H: 4.10%; Found: C: 61.12% H: 4.16%.

EXAMPLE 4

Preparation of 2-phenyl-1,2,3,4-tetrahydroisoquinoline (a) 2-phenylethanol (48.8 g,) and paraformaldehyde (15 g,) were mixed and stirred on an ice bath while a stream of hydrogen chloride gas was passed vigorously through the suspension for 2 hr. The ice-bath was removed and the flow of hydrogen chloride was decreased. The mixture was stirred at room temperature for a further 4 hr. during which time the mixture cleared, after which the reaction mixture stood overnight at room temperature. Aqueous sodium hydroxide solution (100 g/100 ml) was added cautiously, with stirring to the reaction mixture over a period of 30 min. The mixture was heated at reflux for 2 hr., cooled and the oil extracted with ether (3×100 ml). The ether layer was dried (magnesium sulphate) and the solvent removed in vacuo. The residue was distilled under vacuum to give isochroman (45.7 g, b.pt 84.5°–85°/8 mmHg)

(b) Phosphorus pentachloride (62.5 g), was added portionwise with stirring over 30 mins. to methylformate (20 g), at 0°. The reaction mixture was allowed to warm to room temperature and was then warmed to 40° for 30 min. and distilled using a 30 cm spiral coil columm. The main fraction (45 g, b.pt. 92°–97°) was redistilled to give dichloromethyl methylether (21.25 g, b.pt. 85°–85.5°)

(c) Isochroman (20 g,) and dichloromethyl methylether (21.25 g) were mixed and heated at reflux for 2 hr. The reaction mixture was cooled, and a small amount of anhydrous zinc chloride added, when a vigorous reaction ensued and the reaction mixture turned brown. After 10 minutes the flask was replaced on the oil bath and heated at reflux for a further 2 hr. The mixture was left to stand overnight at room temperature and, the product, 2-(2-chloroethyl)benzylchloride was then distilled in vacuo (9.5 g. b.pt. 106°–107°/1.5 mm Hg)

(d) A mixture of 2-(2-chloroethyl)benzyl chloride (19 g), aniline (9.3 g), and triethylamine (22.22 g,) in chloroform (80 ml) was heated at reflux for 6 hrs. The reaction mixture was cooled and washed with 2M sodium hydroxide solution (3×100 ml). The chloroform layer was dried (magnesium sulphate) and evaporated in vacuo. The residue was distilled in vacuo to afford 2-phenyl-1,2,3,4-tetrahydroisoquinoline (6.2 g. b.pt. 112°–113°/0.08–0.1 mmHg) characterised by its nmr spectrum.

EXAMPLE 5

Preparation of 2-phenyl-1,2,3,4-tetrahydroisoquinoline hydrochloride 2-phenyl-1,2,3,4-tetrahydroisoquinoline (0.5 g,) was dissolved in 2M hydrochloric acid (10 ml). The resulting murky solution was cleared by filtering through a pad of diatomaceous earth and freeze-dried when 2-phenyl-1,2,3,4-tetrahydroisoquinoline hydrochloride was obtained as a yellow glass (670 mg) m.pt. 135°–138° characterised by its nmr spectrum.

EXAMPLE 6

Preparation of 1,2,3,4-tetrahydro-2-methyl-2-phenylisoquinolinium iodide 2-phenyl-1,2,3,4-tetrahydroisoquinoline (1.01 g,) was dissolved in acetone (10 ml) and methyl iodide (0.794 g,) was added. The clear solution stood at −20° for 48 hr when t.l.c. indicated the presence of unchanged starting material. A further quantity of methyl iodide (0.3 ml) was added and the reaction mixture was heated at reflux for 3 hrs. The solvent was removed in vacuo and the residue triturated with ether. The resulting solid 1,2,3,4-tetrahydro-2-methyl-2-phenylisoquinolinium iodide was filtered off and dried (1 g). m.pt. softens 190°, melts 195° (decomp.)

Microanalysis: Theory: C: 54.70%; H: 5.12%; N: 3.93% I: 36.18%; Found: C: 54.80%; H: 5.32% N: 3.86%; I: 35.32%.

EXAMPLES 7 to 17

The following compounds were prepared by a method exactly analogous to that used in Example 4

EXAMPLE 7

1,2,3,4-tetrahydro-2-(4-chlorophenyl)isoquinoline

Pale pink solid, m.pt. 66°–71°.

Microanalysis: Theory: C: 73.92%; H: 5.74%; N: 5.74%; Cl: 14.57%; Found: C: 73.62%; H: 5.53% N: 5.63%; Cl: 14.92%.

EXAMPLE 8

1,2,3,4-tetrohydro-2-(4-fluorophenyl)isoquinoline

Off-white solid, m.pt. 78°–80°.

Microanalysis: Theory: C: 79.29%; H: 6.16%; N: 6.16%; Found: C: 78.93%; H: 5.96%; N: 5.93%.

EXAMPLE 9

1,2,3,4-tetrahydro-2-(3,5-dimethylphenyl)isoquinoline

Orange oil, solidified on standing.

Microanalysis: Theory (for $0.4H_2O$): C: 83.54%; H: 8.11%; N: 5.73%; Found: C: 83.87%; H: 8.22% N: 5.16%.

EXAMPLE 10

1,2,3,4-tetrahydro-2-(3-trifluoromethylphenyl)isoquinoline

Pale yellow oil, characterised by its nmr spectrum.

EXAMPLE II 1,2,3,4-tetrahydro-2-(4-methylphenyl)isoquinoline

Pale yellow oil, solidified on standing, characterised by its nmr spectrum

EXAMPLE 12

1,2,3,4-tetrahydro-2-(4-methoxyphenyl)isoquinoline

Off white solid, m.pt. 96°–98°, further characterised by its nmr spectrum.

EXAMPLE 13

1,2,3,4-tetrahydro-2-(2,6-dimethylphenyl)isoquinoline

Oil, solidified on standing, characterised by its nmr spectrum

Microanalysis: Theory (for 0.4H₂O): C: 83.54% H: 8.11%; N: 5.73%; Found: C: 83.97% H: 8.25%; N: 5.03%.

EXAMPLE 14

1,2,3,4-tetrahydro-2-(3,4-dichlorophenyl)isoquinoline

White solid, m.pt. 55°–57°

Microanalysis: Theory: C: 64.7% H: 4.7%; N: 5.0%; Found: C: 64.8% H: 4.76%; N: 4.82%.

EXAMPLE 15

1,2,3,4-tetrahydro-2-(4-hydroxyphenyl)isoquinoline

Off-white solid, m.pt. 125°–130° (decomp)

Microanalysis: Theory: C: 80.0%; H: 6.66%; N: 6.22%; Found: C: 79.84%; H: 6.80% N: 5.79%.

EXAMPLE 16

1,23,4-tetrahydro-2-(2-4-dimethoxyphenyl)isoquinoline

White solid, m.pt 62°–64°

Microanalysis: Theory: C: 75.83% H: 7.06% N: 5.20%; Found: C: 25.59%; H: 6.8% N: 5.13%.

EXAMPLE 17

1,2,3,4-tetrahydro-2-dimethoxyphenyl)isoquinoline

Clear oil

Microanalysis: Theory: C: 75.83%; H: 7.06%; N: 5.20%; Found: C: 75.28%; H: 7.00%; N: 4.76%.

EXAMPLE 18

Preparation of 6-chloro-2-phenyl-1,2,3,4-tetrahydroisoquinoline (a) 3-Chlorophenylbenzyl cyanide (50.0 g) was suspended in water (50 ml) and conc. sulphuric acid was added dropwise to the stirred mixture; followed by glacial acetic acid (50 ml). The mixture was heated at reflux for 1½ hr. and then poured into water (200 ml) with stirring. The solid 3-chlorophenylacetic acid that separated out was filtered and dried. (58.2 g) m.pt. 78°–80°.

(b) Lithium aluminium hydride (19 g,) was suspended in dry ether (300 ml) and 3-chlorophenylacetic acid (58 g,) in dry ether (600 ml) was added dropwise to the stirred suspension over 1 hr. The mixture was then heated at reflux for 2 hr. when tlc indicated completion of reaction. Excess lithium aluminium hydride was carefully decomposed with water (500 ml). The ether layer was separated off and 2M hydrochloric acid was used to break up the gelatinous aqueous layer which was then extracted with ether (2×400 ml). The combined ether layers were washed with water (300 ml), dried (sodium sulphate) and evaporated in vacuo to give 2-(3-chlorophenyl)ethanol as a pale yellow oil (53.1 g) characterised by its nmr spectrum.

(c) 2-(3-Chlorophenyl)ethanol (48.2 g) and paraformaldehyde (10.8 g) were mixed and warmed to 70° on an oil bath. A stream of hydrogen chloride gas was passed vigorously through the suspension for about 7 hr. The reaction mixture was then allowed to stand at room temperature overnight. Aqueous sodium hydroxide solution (100 g/100 ml) was added cautiously to the reaction mixture. After the initial reaction subsided the rest of the alkali solution was run in fast and the resulting mixture was heated at reflux on an oil bath for 2 hr. The reaction mixture was cooled and extracted into ether (3×100 ml). The ether layer was dried (sodium sulphate) and evaporated in vacuo to give the 6-chloroisochroman as an oil (46 g), which was purified by distillation in vacuo (25.1 g, b.pt. 76°–80°/0.6 mmHg), characterised by its nmr spectrum.

(d) 6-Chloroisochroman (25.19 g,) and dichloromethyl methylether (34.5 g) were mixed and heated on an oil bath at 120° for 3 hr. The reaction mixture was allowed to stand at room temperature for 72 hr. A small amount of chloride was added to the reaction mixture when a vigorous reaction ensued and the reaction mixture turned brown. After 10 min. the reaction mixture was again heated at reflux for a further 2 hr. after which it was diluted with water (300 ml and extracted into ether (3×125 ml). The ether extract was washed with sodium hydrogen carbonate solution (10% w/v 3×60 ml) then with water (100 ml) and dried (magnesium sulphate) and evaporated in vacuo to afford 6-chloro-2-(2-chloroethyl)benzyl chloride as a brown oil (31.7 g). This was characterised by its nmr spectrum.

(e) 4-chloro-2-(2-chloroethyl)benzyl chloride (5 g), aniline (2.1 g) and triethylamine (5.7 g), were dissolved in chloroform (40 ml) and the mixture heated at reflux for 18 hr. The reaction mixture was cooled and washed with 2M sodium hydroxide solution (100 ml), 2M hydrochloric acid (100 ml) and water (100 ml), then dried (sodium sulphate) and evaporated to dryness in vacuo. The residue was chromatographed on silica gel to give the product, 6-chloro-2-phenyl-1,2,3,4-tetrahydroisoquinoline m.pt. 67°–70°.

Microanalysis: Theory (for 0.25H₂O): C: 72.72%; H: 5.85% N 5.65%; Found: C: 72.43% H: 5.30% N: 5.50%.

EXAMPLE 19 and 20

The following compounds were prepared by a method exactly analogous to that used in Example 18.

EXAMPLE 19

1,2,3,4-tetrahydro-2-(4-chlorophenyl)-6-chloroisoquinoline

Off-white solid m.pt. 122°–126° (decomp).

Microanalysis: Theory (for 0.25H₂O): C: 63.82%; H: 4.78%; N: 4.96%; Found: C: 63.61%; H: 4.50%; N: 4.84%.

EXAMPLE 20

1,2,3,4-tetrahydro-2-(4-fluorophenyl)-6-chloroisoquinoline

Buff solid, m.pt. 75°–78°

Microanalysis: Theory (for 0.2H₂O): C: 67.9% H: 5.05%; N: 5.28%; Found: C: 68.1%; H: 4.88% N: 5.27%.

EXAMPLE 21

Preparation of 7-chloro-2-phenyl-1,2,3,4-tetrahydroisoquinoline (a) Homophthalic acid (125 g) was added portionwise with stirring to fuming nitric acid (d 1.5, 450 ml) on an ice-bath at such a rate that the temperature did not rise above 22°. The reaction mixture was then stirred at room temperature for 1½ hr. Crushed ice (450 g) was then added at such a rate that the temperature did not rise above 25°. The precipitated solid 4-nitrohomophthalic acid was filtered off and dried (100 g) m.pt. 223°–225° (decomp).

(b) 4-Nitrohomophthalic acid (100 g) was dissolved in methanol (600 ml) and palladium on carbon catalyst (10%, w/v 5 g) was added. The mixture was hydrogenated at 90 atm. pressure until 3 mol equivalent of hydrogen had been absorbed (20 hr.). The thick, pale grey slurry was filtered and washed exhaustively with hot water. The filtrate was concentrated in vacuo to ca 200 ml and refrigerated at +4°. 4-Aminohomophthalic acid separated from solution as a yellow solid which was filtered off and dried at 110° (72 g). m.pt. 300°, characterised by its nmr spectrum.

(c) Sodium nitrite (25.73 g) was added portionwise to a cooled solution (at 0°–5° of 4-aminohomophthalic acid (71.9 g) in conc. hydrochloric acid (500 ml). To the above formed suspension of the diazonium salt a solution of cuprous chloride (46.16 g) in hydrochoric acid solution (36% w/v 100 ml) and water (40 ml) was added at 0°. The precipitated solid, 4-chlorohomophthalic acid, was filtered off and dried at 110° (79.3 g), m.pt. 198°–208, characterised by its nmr spectrum.

(d) 4-Chlorohomophthalic acid (78 g) was dissolved in ethanol (200 ml) and benzene (500 ml) and conc. sulphuric acid (4 ml) was added to the solution. The mixture was heated at reflux using a Dean and Stark apparatus for 48 hrs. when tlc indicated completion of reaction. The solvents were removed in vacuo and the solid, 4-chlorodiethylhomophthalate (75 g), was characterised by its nmr spectrum.

(e) Lithium aluminium hydride (12 g) was suspended in dry ether (500 ml). A solution of diethyl 4-chlorohomophthalate (75 g) in ether (200 ml) was added dropwise to the above suspension over 30 minutes. The reaction mixture was heated at reflux for 2 hrs. Excess lithium aluminium hydride was decomposed carefully with water and the resulting mixture filtered through a pad of diatomaceous earth. The filtrate was partitioned between water (200 ml) and ether (800 ml). The organic layer was dried (magnesium sulphate) and evaporated in vacuo to a semi-solid which on trituration with petroleum ether (b.pt. 40°–60°) gave 2-(4-chloro-6-hydroxymethylphenyl)ethanol as a solid (45 g) m.pt. 75°–76°, characterised by its nmr spectrum.

(f) 2-(4-Chloro-6-hydroxymethylphenyl)ethanol (45 g) was dissolved in orthophosphoric acid (200 ml) and the solution was heated at 100° for 2 hr. The cooled reaction mixture was diluted with water (1 liter), extracted with ether (4×200 ml) and the combined ether extract was washed with sodium hydrogen carbonate solution (10% w/v 2×200 ml) and water (200 ml) and then dried (magnesium sulphate) and decolourised with activated carbon and evaporated in vacuo to afford 7-chloroisochroman as an oil, (30 g), characterised by its nmr spectrum.

(g) 7-Chloroisochroman (30 g) was added to dichloromethylmethylether (23.4 g) and the mixture was heated at 120° for 2 hr. The reaction mixture was cooled and a small amount of anhydrous zinc chloride was added when a vigorous reaction ensued. When the reaction had subsided, the mixture was heated at 120° for a further 2 hr. The reaction mixture was diluted with water (400 ml) and extracted into ether (4×150 ml). The combined ether extract was washed with sodium hydrogen carbonate solution 10% w/v 2×100 ml) then water (2×100 ml), and then dried (magnesium sulphate) and evaporated in vacuo to give 5-chloro-2-(2-chloroethyl)benzyl chloride as a brown oil (32 g) characterised by nmr spectrum.

(h) 5-Chloro-2-(2-chloroethyl)benzyl chloride (8 g), was dissolved in chloroform (50 ml), then aniline (2.79 g,) and triethylamine (8.01 g,) were added to the solution. The mixture was refluxed for 18 hr. then cooled and washed with 2M sodium hydroxide solution (2×100 ml). The chloroform layer was dried (magnesium sulphate) and evaporated in vacuo. The residue was distilled in vacuo to afford 7-chloro-2-phenyl-1,2,3,4-tetrahydroisoquinoline (1.35 g), b.pt. 170°–180°/0.6–0.8 mmHg) characterised by its nmr spectrum.

Microanalysis: Theory (for 0.25H$_2$O): C: 72.72%; H: 5-85%; N: 5.65%; Found: C: 72.58%; H: 5.36%; N: 5.21%.

EXAMPLES 22 and 23

The following compounds were prepared by a method exactly analogous to that used in Example 21

EXAMPLE 22

7-chloro-2-(4-chlorophenyl)-1,2,3,4-tetrahydroisoquinoline

Off-white solid, m.pt. 68°–70°
Microanalysis: Theory: C: 64.7% H: 4.67%; N: 5.03%; Found: C: 64.5%; H: 4.78% N: 5.05%.

EXAMPLE 23

7-chloro-2-(3,4-dichlorophenyl)-1,2,3,4-tetrahydroisoquinoline

Pale yellow solid, m.pt. softens 51°–54°, clears 65°, characterised by its nmr spectrum.

EXAMPLE 24

Preparation of 1,2,3,4-tetrahydro-2-phenylquinoline (a) Quinoline (40 g) was dissolved in dry ether (250 ml) and treated dropwise with a solution of phenyl lithium (160 ml of 1.88 m solution in benzene/ether). The mixture was stirred at room temperature for 18 hr., then washed with aqueous ammonium chloride solution (20% w/v 2×100 ml) and then water (2×100 ml). The aqueous phase was extracted with ether (2×100 ml) and the combined ether layers were dried (magnesium sulphate) and evaporated in vacuo to give an oil. Unreacted quinoline was removed from the product by distillation in vacuo (80°–90°/10–15 mm Hg). A portion of the residue was crystallised from industrial methylated spirit to afford 2-phenylquinoline m.pt. 84°–86° characterised by its nmr spectrum. The bulk of the product was also characterised by its nmr spectrum.

(b) 2-Phenylquinoline (65 g) was dissolved in absolute alcohol (200 ml) and heated to reflux when sodium metal (25 g) was added in portions over 1 hr. The resulting mixture was maintained at reflux for a further 3 hr. The mixture was diluted with water (300 ml) and acidified with conc. hydrochloric acid. The alcohol was removed in vacuo and the residue made basic with 10M sodium hydroxide solution. The resulting solution was extracted with ether (4×150 ml) and the ether layer was dried (magnesium sulphate) and evaporated in vacuo to give an oil which was distilled twice to give the product, 1,2,3,4-tetrahydro-2-phenylquinoline (b.pt. 114°/0.1 mm Hg). This was characterised by its nmr spectrum.

Microanalysis: Theory: C: 86.12%; H: 7.17%; N: 6.69%; Found: C: 86.31%; H: 7.52% N: 6.54%.

EXAMPLE 25

Preparation of 1,2,3,4-tetrahydro-3-phenylquinoline (a) Isatin (14.7 g,) was dissolved in aqueous potassium hydroxide(30% w/v 200 ml) and phenylacetaldehyde (12.1 g,) was added and the mixture heated at reflux for 72 hr. The cooled reaction mixture was extracted with ether. The aqueous layer was acidified with conc. hydrochloric acid. The yellowish-red solid was collected and stirred with aqueous sodium hydrogen carbonate solution (10% w/v 500 ml) for 2 hr. The insoluble solid (isatin) was filtered off and the filtrate acidified with conc. hydrochloric acid when 3-phenylquinoline-4-carboxylic acid separated as a yellow solid which was filtered off and dried (2.8 g) m.pt. 285°–288°.

(b) 3-Phenyl-quinoline-4-carboxylic acid (2.5 g) was heated gently until the evolution of carbon dioxide ceased. The residue was repeatedly extracted with petroleum-ether (40°-60°) and the extract was evaporated in vacuo to a semi-solid, 3-phenylquinoline which was crystallised twice from petroleum-ether (40°-60°) )(0.6 g), m.pt. 53°–54°. This was characterised by its nmr spectrum.

(c) 3-phenylquinoline (0.5 g) was dissolved in refluxing absolute alcohol (25 ml) and sodium metal (0.28 g) was added portionwise over 30 min. The reaction mixture was then refluxed for 3 hr. The cooled reaction mixture was diluted with water and acidified with conc. hydrochloric acid, the ethanol was removed in vacuo. The reaction mixture was basified with 10M sodium hydroxide solution and extracted with chloroform (2×100 ml). The chloroform extract was dried (magnesium sulphate), decolorised with activated charcoal and evaporated in vacuo to give 1,2,3,4-tetrahydro-3-phenylquinoline as a semi-solid which was crystallised from petroleum-ether (40°-60°), as an off-white solid, m.pt. 84°–86°, characterised by its nmr spectrum.

Microanalysis: Theory: C. 86.12%; H: 7.17%; N: 6.69%; Found: C: 86.11%; H: 6.94%; N:6.52%.

EXAMPLE 26

Preparation of 3-phenyl-1,2,3,4-tetrahydroisoquinoline (a) Benzylphthalide (100 g) was dissolved in aqueous potassium hydroxide solution (33% w/v 400 ml) and the mixture heated at 150° for 3½ hr. The water formed in the reaction was distilled off and collected. The temperature was slowly raised to 212° and maintained there for a further 3 hr. A total of 380 ml of water was collected and the residue solidified. The reaction mixture was cooled on an ice-bath and carefully acidified with conc.hydrochloric acid. The solid trans-stilbene-2-carboxylic acid was filtered off and recrystallised from ethanol, (62 g), m.pt. 188°–161°.

(b) To a stirred solution of trans-stilbene-2-carboxylic acid (88 g) in acetic acid (1.5 litre) on an ice-bath was added rapidly yet dropwise a solution of bromine (72 g) in acetic acid (400 ml). The ice-bath was removed and the acetic acid allowed to melt. The reaction mixture was then filtered and the filtrate diluted with water (3 liters). Trans-3-phenyl-4-bromodihydroisocoumarin, which separated from the solution as a brown oil and solidified on standing overnight, was filtered and dried in an oven (71 g). m.pt. 97°–100°.

(c) Trans-3-phenyl-4-bromodihydroisocoumarin (71 g) was heated on an oil bath at 190° until all effervescence had ceased. The clear brown oil, 3-phenylisocoumarin, was allowed to cool and solidify and then crystallised from ether, (40 g), m.pt. 89°–90°.

(d) 3-Phenylisocoumarin (20 g) was dissolved in ethanol (500 ml) and ammonia solution (200 ml) was added and the mixture heated at reflux for 48 hrs and then left for 18 hrs at +4°.3-Phenylisoquinoline separated out and was filtered and dried, (12.1 g), m.pt. 208°–212°.

(e) 3-Phenylisoquinoline (5 g) was dissolved in dry toluene (250 ml) and phosphorus oxychloride (16.52 g) was added and the mixture was heated at reflux for 48 hr, more phosphorus oxychloride (4 g) being added after 24 hr. The solvent was removed in vacuo to give 1-chloro-3-phenylisoquinoline as an oil which solidified on standing (4 g), characterised by its nmr spectrum. (A small portion was recrystallised from methanol, m.pt. 75°–77°).

Microanalysis: Theory: C: 75.15%; H: 4.17%; N: 5.84%; Cl: 14.82%; Found: C: 75.69% H: 4.11% N: 5.88% I: 14.91%.

(f) 1-Chloro-3-phenylisoquinoline (2.8 g) was dissolved in absolute alcohol (200 ml) and the solution was heated at reflux while sodium metal (2.4 g) was added in portions. It was maintained at reflux for a further 2 hr., when tlc indicated incomplete reaction. Further sodium metal (2.4 g) was added then, and again (2.4 g)after another 6 hr., the heating being continued for 12 hr. in tote. The ethanol was evaporated in vacuo to give an oil which was partitioned between ether and 2M hydrochloric acid. The aqueous layer was separated, basified with 2M sodium hydroxide solution and extracted with ether (2×150 ml). The ether layer was dried (magnesium sulphate) and evaporated in vacuo to give an oil (2.6 g). This was purified by column chromatography on silica gel and 3-phenyl-1,2,3,4-tetrahydroisoquinoline was eluted with dichloromethane/methanol characterised by its nmr spectrum.

Microanalysis: Theory: C: 85.39%; H: 7.25%; N: 6.59%; Found: C: 85.28%; H: 6.95%; N: 6.40%.

EXAMPLE 27

Preparation of isoflavan (a) Phenol (47.9 g) was dissolved in dichloromethane (250 ml) and pyridine (44.3 g). Phenylacetyl chloride (78.8 g) was added with stirring over 40 min., and the resulting mixture allowed to stand at room temperature for 1 hr. The mixture was washed sequentially with water, twice with dilute hydrochloric acid, once with dilute sodium hydroxide solution, and then once with saturated brine. The solution was dried and evaporated to give phenyl phenylacetate 103.3 g., m.pt 39°–41°.

(b) Phenyl phenylacetate (103.3 g) was mixed with aluminium chloride (133.0 g) and the mixture heated at 100° for 1.5 hr. The mixture was cooled and decomposed with ice and concentrated hydrochloric acid. The product was extracted into chloroform and the solution washed with water, extracted with 2M sodium hydroxide solution (2×250 ml) and water, dried, and evaporated. The residual oil was distilled, (b.pt. 110°–115°/0.1 mm Hg) to yield benzyl 2-hydroxyphenyl ketone, (30.1 g) m.pt. 50°55°.

(c) Benzyl-2-hydroxyphenyl ketone (29.0 g) and formamide (29.0 g). were heated together at 208° for 1 hr. The reaction mixture was cooled and diluted with water. The oily product was extracted into chloroform and the solution washed with water, dried and evaporated. The residue was chromatographed on alumina, eluting with toluene, and the product recrystallised once from petroleum ether (80°–100°) and once from toluene to yield isoflavone (3.55 g), m.pt. 132°–134°

(d) Isoflavone (3.00 g) was dissolved in acetic acid (100 ml), and the solution hydrogenated at 50°-60° and 10.4–13.8 atm using 10% w/v palladium or carbon catalyst. The solution was filtered and evaporated, and the residue chromatographed on alumina, eluting with toluene. The product thus obtained gave, on recrystallisation from petroleum ether, (60°-80°) isoflavanone, 0.90 g., m.pt 73°-76°.

(e) Isoflavanone (0.90 g) was dissolved in a mixture of acetic acid (15 ml) and concentrated hydrochloric acid (1.5 ml). and the solution added to zinc amalgam prepared from zinc powder (2.5 g) and mercuric chloride (0.25 g). The mixture was stirred for 45 min., then allowed to stand at room temperature for 18 hrs. The mixture was filtered and the filtrate diluted with water. The precipitated oil was extracted into toluene and the extract washed with saturated sodium hydrogen bicarbonate solution, dried, and evaporated. The residue was chromatographed on alumina, eluting with petroleum ether, (60°-80°) to give, on evaporation of the eluate, pure isoflavan, 0.23 g., m.pt. 54°-56°.

Microanalysis: Theory: C: 85.68% H: 6.71%; Found: C: 85.64% H: 6.72%.

EXAMPLE 28

By a method exactly analogous to that used in Example I, 6-chloro-1-thioflavan may be produced.

EXAMPLES 29 to 31

By a method exactly analogous to that used in Example 24, the following compounds may be produced

| EXAMPLE | COMPOUND |
|---------|----------|
| 29 | 2-(4-chlorophenyl)-1,2,3,4-tetrahydroquinoline |
| 30 | 6-chloro-2-phenyl-1,2,3,4-tetrahydroquinoline |
| 31 | 6-chloro-2-(4-chlorophenyl)-1,2,3,4-tetrahydroquinoline |

EXAMPLES 32 to 34

By a method exactly analogous to that used in Example 28, the following compounds may be prepared:

| EXAMPLE | COMPOUND |
|---------|----------|
| 32 | 2-(4-chlorophenyl)tetralin |
| 33 | 6-chloro-2-phenyltetralin |
| 34 | 6-chloro-2-(4-chlorophenyl)tetralin |

EXAMPLES 35 to 37

By a method exactly analogous to that used in Example 25, the following compounds may be prepared.

| EXAMPLE | COMPOUND |
|---------|----------|
| 35 | 3-(4-chlorophenyl)-1,2,3,4-tetrahydroquinoline |
| 36 | 6-chloro-3-phenyl-1,2,3,4-tetrahydroquinoline |
| 37 | 6-chloro-3-(4-chlorophenyl)-1,2,3,4-tetrahydroquinoline |

EXAMPLES 38 to 40

By a method exactly analogous to that used in Example 26, the following compounds may be prepared.

| EXAMPLE | COMPOUND |
|---------|----------|
| 38 | 3-(4-chlorophenyl)-1,2,3,4-tetrahydroisoquinoline |
| 39 | 6-chloro-3-phenyl-1,2,3,4-tetrahydroisoquinoline |
| 40 | 6-chloro-3-(4-chlorophenyl)-1,2,3,4-tetrahydroisoquinoline |

EXAMPLES 41 to 43

By a method exactly analogous to that used in Example 27 the following compounds may be prepared.

| EXAMPLE | COMPOUND |
|---------|----------|
| 41 | 3-(4-chlorophenyl)chroman |
| 42 | 6-chloro-3-phenylchroman |
| 43 | 6-chloro-3-(4-chlorophenyl)chroman |

EXAMPLE 44

Assay of activity of compounds of formula (I)

Activity may be detected by the plaque inhibition (PI) test and measured by the plaque reduction (PR) test. Both assays involve the formation of a monolayer cell culture in a petri dish followed by infection with a virus suspension, and then overlaying the culture with nutrient agarose in the form of a gel. This gel ensures that there is no spread of virus throughout the culture and thus areas of localised cell destruction, or plaques, are formed.

In the plaque inhibition test a filter paper disc which holds 0.01 ml when impregnated with a solution of compound is placed on top of the agarose gel. The compound may then diffuse throughout the gel so that its greatest concentration will be around the disc and its lowest concentration towards the periphery of the petri dish. The efficacy of the compound may be detected by observing the zone of inhibition of plaque formation.

Detectable activity is measured with the plaque reduction assay. A range of concentrations of compound of known molarity are incorporated in the nutrient agarose overlay. Plaque suppression is proportional to compound concentration. Plaque numbers are expressed as percentages of a control, and a dose response curve may be drawn. From this curve 50% of the effective dose($ED_{50}$) may be estimated.

| RESULTS Activity versus rhinovirus serotype 1B | |
|---|---|
| Compound of Example No | PR($ED_{50}$, µM) |
| 1 | 0.028 |
| 3 | 0.044 |
| 4 | 0.07 (0.017) |
| 7 | 0.10 |
| 8 | 0.21 |
| 11 | 1.00 |
| 12 | 2.45 (1.3) |
| 13 | 0.075 |
| 15 | 1.85 |
| 16 | 8.00 |
| 18 | 0.57 |
| 19 | 0.05 |
| 20 | 0.21 |
| 21 | 0.11 |
| 22 | 0.13 |
| 23 | 0.62 |
| 24 | 0.33 |
| 26 | 0.29 |
| 27 | 0.82 |

EXAMPLES 46 to 136

The following compositions were prepared according to the techniques known in the art of pharmacy.

EXAMPLE 45

An inhalant for use in an insufflator was prepared from the following ingredients
4',6-dichlorothiaflavan: 0.6 g
isopropylmyristate: 10 g
Tween 80: 0.5 g
Span 80: 0.5 g
methyl-p-hydroxy benzoate: 0.1 g
Water: to 100 ml

EXAMPLE 46

A suspension for use as nose drops was prepared from the following ingredients
2-phenyl-1,2,3,4-tetrahydroisoquinoline: 0.6 g
Keltrol: 0.1 g
Sodium Chloride: 0.5 g
Sodium lauryl sulphate: 0.1 g
Methyl-p-hydroxybenzoate: 0.1 g
Water: to 100. ml

EXAMPLE 47

Capsule 1

6-chloro-2-(4-chlorophenyl)-1,2,3,4-teterahydroisoquinoline: 6 g
Spray-dried lactose: 300 g.
Gelatin capsules (size 0) were each filled with 500 mg. of the formulation, affording 10 mg. of active ingredient per capsule.

EXAMPLE 48

Capsule 2

2-phenyltetralin: 6 g
Spray-dried lactose: 208 g
Maize starch: 20.8 g
Polyvinylpyrollidine: 5.2 g
Gelatin capsules (size 1) were each filled with 400 mg. of the formulation, affording 10 mg. of the active ingredient per capsule.

EXAMPLE 49

Tablet of 6-chloro-2-(4-chlorophenyl)-1,2,3,4-tetrahydroisoquinoline

A tablet formulation containing a mixture of the title compound (10 mg), lactose (90 mg), maize starch (10 mg) and magnesium sterate (1 mg) is prepared by wet granulation.

EXAMPLE 50 to 92

Tablet formulations each containing one of the flavan derivatives of Examples 1 to 18 and 20 to 43 are prepared by a method exactly analogous to that used in Example 51 1

EXAMPLE 93

Oil formulation of 6-chloro-2-(4-chlorophenyl)-1,2,3,4-tetrahydroisoquinoline 6-chloro-2-(4-chlorophenyl)-1,2,3,4-tetrahydroisoquinoline: 1 g.
Olive oil B.P.: 1 g.

The compound was dissolved in olive oil for use by oral administration.

EXAMPLE 94 to 136

Oil formulations each containing one of the compounds of Examples 1 to 18 and 20 to 43 are prepared by a method exactly analogous to that used in Example 93.

EXAMPLE 137

Preparation of 2-phenyltetralin (a) 2-Tetralone (8.76 g) in dry ether (100 ml) was added dropwise to phenyl magnesium bromide (generated from bromobenzene 19.16 g) in dry ether (300 ml). The mixture was refluxed for 1 hr. The reaction mixture was decomposed by careful addition of water. The resulting emulsion was clarified by addition 2M-hydrochloric acid (250 ml) and ether (500 ml). The ether layer was separated and washed with water (100 ml), dilute sodium hydrogen carbonate solution solution (200 ml) and water (100 ml) and dried (magnesium sulphate and evaporated in vacuo to afford 2-hydroxy-2-phenyl-1,2,3,4-tetrahydronaphthalene as an oil. (8.8 g), characterised by its nmr spectrum (b) 2-hydroxy-2-phenyl-1,2-3,4-tetrahydronaphthalene (8.5 g) was heated at 180°–200° with potassium hydrogen sulphate (40 g) for 18 hr. The mixture was extracted with ether ($7 \times 80$ ml). The ether extract was dried (magnesium sulphate) and evaporated in vacuo to give 2-phenylnaphthalene as an oil which solidified on standing and was recrystallised from ether/petroleum 40°–60°) ) (5.7 g) m.pt. 92°–94° and characterised by its nmr spectrum.

(c) 2-phenylnapthalene (5.66 g) was dissolved in absolute alcohol (100 ml) and catalyst (10% w/w palladium on carbon 10.5 g) was added. The mixture was hydrogenated at 80 atm./70° for 6 hr. The catalyst was filtered off the cooled reaction mixture and, on evaporation the filtrate gave an oil (5.2 g). The 2-phenyltetralin so obtained was distilled in vacuo (b.pt. 115°/0.33 mm Hg, 1.8 g) and characterised by its nmr spectrum.

Microanalysis: Theory: (for 0.25 $H_2O$): C: 90.3% H: 7.76%; Found: C: 90.85% H: 8.09%.

EXAMPLES 138 to 142

Formulations of the compound of Example 138 were prepared by methods analogous to those of Example 45, 46, 47, 49, and 93.

EXAMPLE 143

Intranasal Administration-Simulation in vitro

Petri dishes were prepared, as for the plaque inhibition test and the confluent sheet of cells was covered with a layer of agarose gel. The compound, 2-phenyltetrahydroisoquinoline (1 µg) was dissolved in ethanol, and applied to the lids of the petri dishes. When the ethanol had evaporated, leaving the compound spread over the inside of the lids, these were replaced on the petri dishes. Sufficient compound penetrated the agarose layer to cause total inhibition of plaque formation.

EXAMPLE 144

Preparation of 6-chlorothioflavan (a) 3-Phenyl-3-(4-chlorophenylthio) propionic acid was prepared by a method exactly analogous to that used in Example 1(a). It was recrystallised from 80°–100° petroleum ether and had m.pt. 90°–92°.

(b) 6-Chlorothioflavanone was prepared by a method exactly analogous to that used in Example 2(b). It was recrystallised from ethanol and had a m.pt. 90°–91°.

(c) 6-Chlorothioflavan m.pt. 91°–93° was prepared by a method exactly analogous to that used in Example 1(c). It was recrystallised from ethanol and gave a yield of 49%

Microanalysis: Calculated: C: 69.09% H: 5.02%; Found: C: 69.35% H: 5.10%.

We claim:

1. A method for the treatment of a rhinoviral infection in a human being or other animal suffering from a rhinoviral infection which comprises the intranasol administration of an effective, non-toxic antirhinoviral dosage of a compound of formula (III)

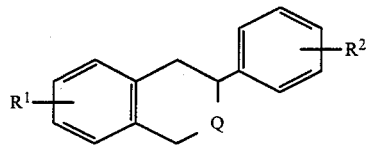

wherein Q is a sulphur atom or an $NR^3$ group, and $R^1$ represents four substituents and $R^2$ represents five substituents, each of said substituents being selected from hydrogen or halogen atoms, (lower)alkyl, hydroxy(lower)alkyl, carboxy(lower)alkyl, (lower)alkoxy, amino, (lower)alkylamino, di(lower)alkylamino, acylamino, nitro, cyano, trifluoromethyl, carboxyl, methylene-dioxy and hydroxyl groups, and whenever present $R^3$ is selected from (lower)alkyl groups and hydrogen atoms, or a pharmaceutically acceptable salt or ester thereof where appropriate.

2. A method for the treatment of rhinoviral infections in a human being or other animal suffering from a rhinoviral infection which comprises the intranasol administration of an effective, non-toxic antirhinoviral dosage of a compound of formula (IV)

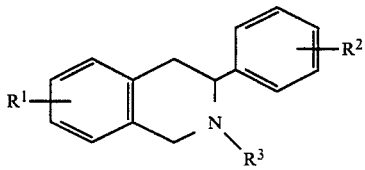

wherein $R^1$ represents four substituents and $R^2$ represents five substituents, each of said substituents being selected from hydrogen or halogen atoms, (lower)alkyl, hydroxy(lower)alkyl, carboxy(lower)alkyl, (lower)alkoxy, amino, (lower)alkylamino, di(lower)alkylamino, acylamino, nitro, cyano, trifluoromethyl, methylene-dioxy and hydroxyl groups, and $R^3$ is selected from (lower)alkyl groups and hydrogen atoms, or a pharmaceutically acceptable salt or ester thereof where appropriate.

3. A method according to claim 2 wherein $R^1$ in the compound of formula (IV) represents four substituents and $R^2$ represents five substituents selected from hydrogen or halogen atoms, and amino, hydroxyl, methyl, ethyl, methoxyl, ethoxyl, hydroxy methyl, trifluoromethyl and cyano groups.

4. A method according to claim 2 or claim 3 wherein at least two of the substituents represented by $R^1$ in the compound of formula (I) and/or at least three of the substituents represented by $R^2$ are hydrogen atoms.

5. A method according to claim 4 wherein substituents other than hydrogen atoms represented by $R^1$ in the compound of formula (I) are located at the 6 and/or 7 positions of a compound of formula (I) and substituents other than hydrogen atoms represented by $R^2$ are located at the 3', 4' and/or 5' positions.

6. A method for the treatment of rhinoviral infections in a human being or other animal suffering from a rhinoviral infection, which comprises the intranasol administration of an effective, non-toxic antirhinoviral dosage of a compound of formula (IVA)

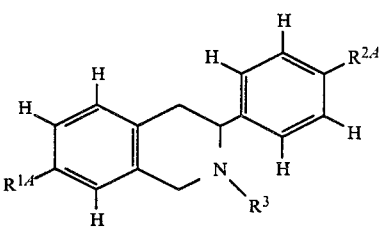

wherein $R^3$ is selected from (lower)alkyl groups and hydrogen atoms and $R^{1A}$ and $R^{2A}$ each represent a single substituent selected from hydrogen or halogen atoms, (lower)alkyl, hydroxy(lower)alkyl, carboxy(lower)alkyl, (lower)alkoxyl, amino, (lower)alkylamino, di(lower)alkylamino, acylamino, nitro, cyano, trifluoromethyl, carboxyl, methylene-dioxy and hydroxyl groups, or salt or ester thereof where appropriate.

7. A method for the treatment of a rhinoviral infection in a human being or other animal suffering from a rhinoviral infection, which comprises the intransasol administration of an effective, non-toxic antirhinoviral dosage of 6-chloro-3-(4-chlorophenyl)-1,2,3,4-tetrahydroisoquinoline, or a pharmaceutically acceptable salt thereof.

8. A method according to claim 2, or claim 6, or claim 7 wherein the compound of formula (IV) or (IVA) is administered in a dosage of from about 2 µg to about 10 mg/kg of animal body weight per day.

9. A method according to claim 8 wherein the compound of formula (IV) or (IVA) is administered in a dosage of from about 25 µg to about 1 mg/kg of animal body weight per day.

10. A method according to claim 2, or claim 6, or claim 7 wherein the compound of formula (IV) or (IVA) is administered as a pharmaceutical composition comprising an effective, non-toxic, antirhinoviral dosage of a compound of formula (IV) or (IVA) together with a pharmaceutically acceptable carrier therefor.

11. A pharmaceutical composition comprising a an effective antirhinoviral amount of compound of formula (V)

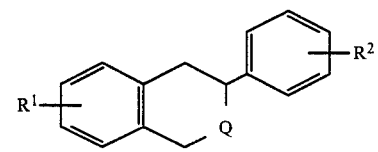

wherein Q is a sulphur atom or an $NR^3$ group, and $R^1$ represents four substituents, and $R^2$ represents five substituents, each of said substituents being selected from hydrogen or halogen atoms, (lower)alkyl, hydroxy(lower)alkyl, carboxy(lower)alkyl, (lower)alkoxy, amino, (lower)alkylamino, di(lower)alkylamino, acylamino, nitro, cyano, trifluoromethyl, carboxyl, methylene-dioxy and hydroxyl groups, and whenever present $R^3$ is selected from (lower)alkyl groups and hydrogen atoms, or a pharmaceutically acceptable salt or ester thereof where appropriate, together with a pharmaceutically carrier therefor.

12. A pharmaceutical composition comprising a an effective antirhinoviral amount of compound of formula (IV)

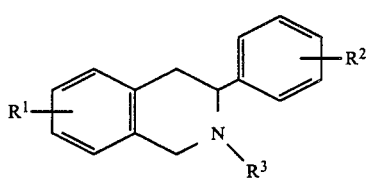
(VI)

wherein $R^1$ represents four substituents and $R^2$ represents five substituents, each of said substituents being selected from hydrogen or halogen atoms, (lower)alkyl, hydroxy(lower) alkyl, carboxy(lower)alkyl, (lower)alkoxy, amino, (lower) alkylamino, di(lower)alkylamino, acylamino, nitro, cyano, trifluoromethyl, carboxyl, methylene-dioxy and hydroxyl groups and $R^3$ is selected from (lower)alkyl groups and hydrogen atoms, or a pharmaceutically acceptable salt or ester thereof where appropriate, together with a pharmaceutically acceptable carrier therefor.

13. A pharmaceutical composition according to claim 12 which comprises a compound of formula (IV) or (IVA) as defined in any one of claims 3 to 6 or a pharmaceutically acceptable salt or ester thereof where appropriate together with a pharmaceutically acceptable carrier therefor.

14. A pharmaceutical composition comprising an effective antirhinoviral amount of 6-chloro-3-(4-chlorophenyl)-1,2,3,4-tetrahydroisoquinoline, or a pharmaceutically acceptable salt thereof, together with a pharmaceutically acceptable carrier therefor.

15. A method of inhibiting a rhinovirus reproduction in living cells which comprises applying to said cells containing said virus an effective rhinovirus reproduction inhibition amount of the compound 6-chloro-3-(4-chlorophenyl)-1,2,3,4-tetrahydroisoquinoline or a pharmaceutically acceptable salt thereof.

16. A method of inhibiting rhinovirus reproduction comprising contacting rhinovirus with an effective rhinovirus reproduction inhibition amount of the compound 6-chloro-3-(4-chlorophenyl)-1,2,3,4,-tetrahydroisoquinoline or a pharmaceutically acceptable salt thereof.

17. A method of inhibiting rhinovirus reproduction in living cells which comprises applying to said cells containing said virus an effective rhinovirus reproduction inhibition amount of the compound of 6-chloro-3-(4-chlorophenyl)-1,2,3,4-tetrahydroquinoline or a pharmaceutically acceptable salt thereof.

18. A method of inhibiting rhinovirus reproduction comprising contacting rhinovirus with an effective rhinovirus reproduction inhibition amount of the compound 6-chloro-3-(4-chlorophenyl)-1,2,3,4-tetrahydroquinoline or a pharmaceutically acceptable salt thereof.

* * * * *